(12) United States Patent
Klaubert et al.

(10) Patent No.: US 6,852,504 B2
(45) Date of Patent: Feb. 8, 2005

(54) METHOD FOR MEASURING CELLULAR TRANSMEMBRANE POTENTIAL CHANGES

(75) Inventors: Dieter Klaubert, Arroyo Grande, CA (US); Zhenjun Diwu, Sunnyvale, CA (US); Guoliang Yi, Sunnyvale, CA (US); Martin Kirk, San Carlos, CA (US)

(73) Assignee: Molecular Devices Corporation, Sunnyvale, CA (US)

( * ) Notice: Subject to any disclaimer, the term of this patent is extended or adjusted under 35 U.S.C. 154(b) by 422 days.

(21) Appl. No.: 09/924,797

(22) Filed: Aug. 8, 2001

(65) Prior Publication Data

US 2003/0087332 A1 May 8, 2003

(51) Int. Cl.$^7$ ................................................. C12Q 1/02
(52) U.S. Cl. ............................ 435/29; 435/34; 544/242
(58) Field of Search ........................... 544/242; 435/29, 435/34, 173.4, 968; 436/172

(56) References Cited

U.S. PATENT DOCUMENTS

| | | | |
|---|---|---|---|
| 4,370,401 A | | 1/1983 | Winslow et al. |
| 6,287,758 B1 | * | 9/2001 | Okun et al. .................... 435/4 |
| 6,455,271 B1 | | 9/2002 | Little, II et al. |
| 6,537,771 B1 | * | 3/2003 | Farinas et al. ................ 435/29 |
| 6,596,522 B2 | * | 7/2003 | Tsien et al. ............... 435/173.4 |

OTHER PUBLICATIONS dePoorter L. Convenient Flourescence Based Methods to Measure Membrane Potential and Intracellular pH in the Archaeon M. thermoautotrophicum. J of Microbiological Methods Feb. 2001. 47(2)233–241.*
Wu J–Y, Cohen L B., Fast Multisite Optical Measurement of Membrane Potential. In *Fluorescent and Luminescent Probesfor Biological Activity*, Mason W T, Ed., pp. 389–404 (1993).
Bartsch et al., (1982) *Arch. Pharm.*, 315:761–766, abst only.
Beck, (1997) *FEMS Micro. Letters*, 147:11–14.
Bronner C. et al., (1991) *Biochim Biophys Acta* 1070:321–331.
dePoorter, et al., (2001) *J. Microbiol. Methods*, 47:233–241.
Fischer, (1969) *Chem Ber*, 102:2609–2620, German.

Freedman JC, et al. (1989) *Methods Enzymol* 172:102–122.
Gonzalez, et al. (1997) *Chem Biol* 4:269–277.
Gross D, et al. (1989) *Methods Cell Biol* 30:193–218.
Lee et al., (1999) *J. Korean Med Science*, 14:21–26.
Liao et al., (1999) *Antimicrobial Agents and Chemotherapy* 43:1034–1041.
Loew (1993) *Methods in Cell Biology*, 38:195–209.
Loew et al., (1994) *Adv Chem Ser* 235:151.
Loew LM. (1999) *Fluorescent and Luminescent Probes for Biological Activity*, Mason WT, $2^{nd}$ Ed. pp. 210–221.
Nakashima, et al., (1992) *Biomed. Chromatography* 6:55–58.
Plasek, et al. (1996) *J Photochem Photobiol B* 33:101–124.
Sabry et al, (2000) *J. of Pharm. Biomed. Analysis* 22:257–264.
Shapiro, (1994) *Methods Cell Biol.* 41:121–133.
Smith JC. (1990) *Biochim Biophys Acta* 1016:1–28.
Zochowski, et al., (2000) *Biol Bull* 198:1–21.
International Search Report for International Patent Application PCT/US02/25046.

* cited by examiner

*Primary Examiner*—Ralph Gitomer
(74) *Attorney, Agent, or Firm*—Kolisch Hartwell, P.C.

(57) ABSTRACT

The invention encompasses an improved method for measuring membrane potential using compounds of the formula I as potentiometric probes. These probes may be used in combination with other fluorescent indicators such as Indo-1, Fura-2, and Fluo-3, such probes may be used in microplate reading devices such as FLIPR™, fluorescent imaging plate reader, sold by Molecular Device Corp., of Sunnyvale, Calif.; flow cytometers; and fluorometers. Such probes are used to measure membrane potential in live cells

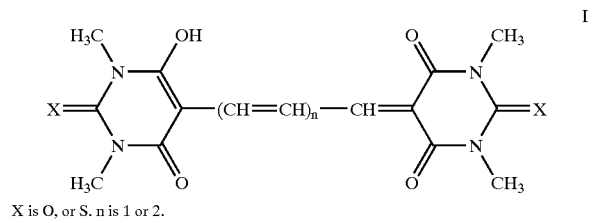

X is O, or S. n is 1 or 2.

10 Claims, 4 Drawing Sheets

METHOD FOR MEASURING CELLULAR TRANSMEMBRANE POTENTIAL CHANGES

BACKGROUND OF THE INVENTION

1. Field of the Invention

The present invention relates generally to the fields of biology and chemistry, and bioanalytical instrumentation. In particular, the present invention is directed to composition and methods for use in sensing membrane potentials, especially in biological systems. Potentiometric optical probes enable researchers to perform membrane potential measurements in organelles and in cells that are too small to allow the use of microelectrodes. Moreover, in conjunction with imaging techniques, these probes can be employed to map variations in membrane potential across excitable cells and perfused organs with spatial resolution and sampling frequency that are difficult to achieve using microelectrodes.

2. Background of the Art

The plasma membrane of a cell typically has a transmembrane potential of approximately −70 mV (negative inside) as a consequence of $K^+$, $Na^+$ and $Cl^-$ concentration gradients that are maintained by active transport processes. Potentiometric probes offer an indirect method of detecting the translocation of these ions. Increases and decreases in membrane potential (referred to as membrane hyperpolarization and depolarization, respectively) play a central role in many physiological processes, including nerve-impulse propagation, muscle contraction, cell signaling and ion-channel gating (references 1–3). Potentiometric probes are important tools for studying these processes, and for cell-viability assessment. Potentiometric probes include the cationic or zwitterionic styryl dyes, the cationic carbocyanines and rhodamines, the anionic oxonols and hybrid oxonols and merocyanine 540 (references 4–8). The class of dye determines factors such as accumulation in cells, response mechanism and toxicity. Mechanisms for optical sensing of membrane potential have traditionally been divided into two classes: sensitive but slow redistribution of permanent ions from extracellular medium into the cell, and fast but small perturbation of relatively impermeable dyes attached to one face of the plasma membrane (references 2 and 3).

The bis-barbituric acid and thiobarbituric oxonols, often referred to as DiBAC and DiSBAC dyes respectively, form a family of spectrally distinct potentiometric probes with excitation maxima covering most of the range of visible wavelengths. $DiBAC_4(3)$ and $DiSBAC_2(3)$ have been the two most popular oxonol dyes for membrane potential measurement (references 9 and 11). These dyes enter depolarized cells where they bind to intracellular proteins or membranes and exhibit enhanced fluorescence and red spectral shifts. Increased depolarization results in more influx of the anionic dye and thus an increase in fluorescence. $DiBAC_4(3)$ reportedly has the highest voltage sensitivity. The long-wavelength $DiSBAC_2(3)$ has frequently been used in combination with the UV light-excitable $Ca^{2+}$ indicators Indo-1 or Fura-2 for simultaneous measurements of membrane potential and $Ca^{2+}$ concentrations. Interactions between anionic oxonols and the cationic $K^+$-valinomycin complex complicate the use of this jonophore to calibrate potentiometric responses. DIBAC and DiSBAC dyes are excluded from mitochondria because of their overall negative charge, making them superior to carbocyanines for measuring plasma membrane potentials.

In general, DiBAC and DiSBAC dyes bearing longer alkyl chains had been proposed to have better properties for measuring membrane potentials (references 5 and 12). $DiSBAC_6(3)$ has been selected to use in a FRET-based membrane potential assay (reference 12). There are no reports on $DiBAC_1$ and $DiSBAC_1$ for measuring membrane potential.

It has been discovered that $DiBAC_1(3)$ and $DiSBAC_1(3)$ possess unexpected properties that can be used to measure membrane potentials with FLIPR and other fluorescence devices. Compared with other members of the DiBAC and DiSBAC family, $DiBAC_1(3)$ and $DiSBAC_1(3)$ give stronger signal and faster response besides its better water solubility.

SUMMARY OF THE INVENTION

The invention encompasses an improved method for measuring membrane potential using compounds of the formula I as potentiometric probes. These probes may be used in combination with other fluorescent indicators such as Indo-1, Fura-2, and Fluo-3, calcium green or Fluo-4. Such probes may be used in microplate reading devices such as FLIPR, fluorescent imaging plate reader, sold by Molecular Devices Corp., of Sunnyvale, Calif.; flow cytometers; and fluorometers. Such probes are used to measure membrane potential in live cells.

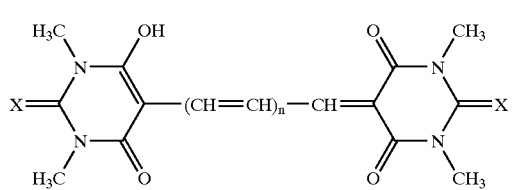

Wherein X is O, or S; n is 1 or 2.

The invention also encompasses test kits containing reagents of compound I, compound I in combination with another fluorescent reagent and in particular fluorescent indicators such as Indo-1, Fura-2, Fluo-3, calcium green or Fluo-4.

Another aspect of the invention involves a method for generating voltage sensitive fluorescent changes comprising incubating the membrane with:

(a) A first reagent selected from the potentiometric probes which redistribute from one side of the membrane to the opposite side in response to tranemembrane potential; and a second reagent selected from the group consisting of non-fluorescent dyes or pigments that are not membrane-permeable, and undergo energy transfer with the first reagent on one side of the membrane to reduce or eliminate the fluorescence signal on that side; or (b) A first reagent selected from the potentiometric probes which redistribute from one side of the membrane to the opposite side in response to transmembrane potential; and a second reagent selected from the group consisting of non-fluorescent dyes or pigments that are not membrane-permeable, and absorb the excitation light or emission from the first reagent on one side of the membrane to reduce or eliminate the undesired fluorescence signal; or (c) A first reagent selected from the potentiometric probes which redistribute from one side of the membrane to the opposite side in response to transmembrane potential; and a second reagent selected from the group consisting of fluorescent or luminescent probes which undergo energy transfer with the first reagent, said second reagent being located adjacent to either the one side or the other side of the membrane.

DETAILED DESCRIPTION OF THE INVENTION

Figure 1:
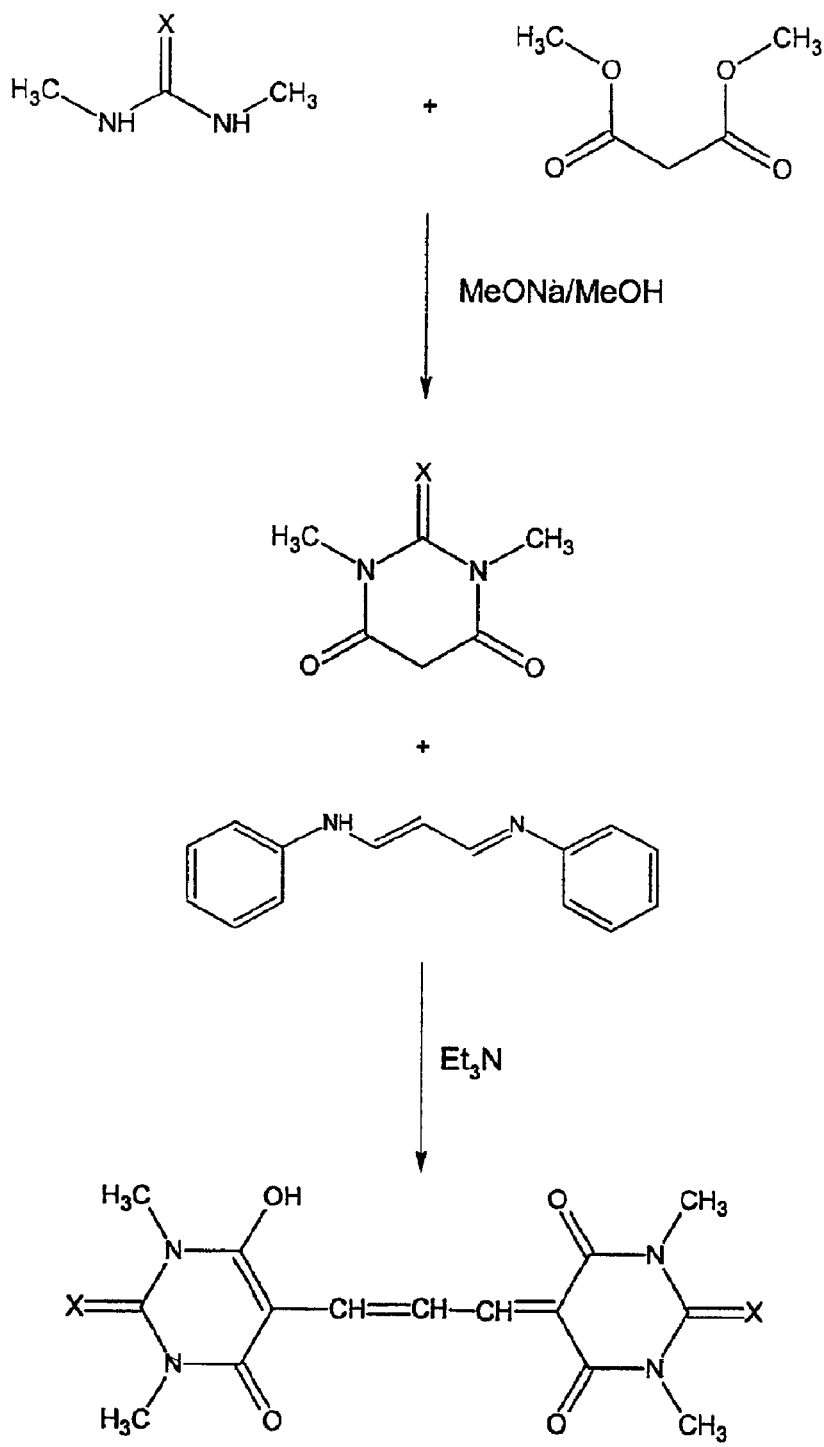
FIG. 1 is a reaction scheme for making DiBAC and DiSBAC.

Compounds useful in practicing the present invention are made according to methods described by G. W. Fischer in Chem Ber, 1969, 102:2609–2620, as shown in FIG. 1.

The invention is illustrated by the following examples:

EXAMPLE 1

Preparation of $DiSBAC_1(3)$

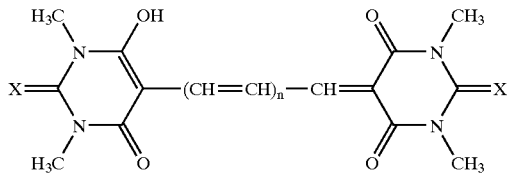

DiBAC and DiSBAC dyes are prepared based on the procedure for ethyl and butyl derivatives (H. Bartech and G. Haubold, Arch. Pharm. 1982, 315, 761–766). Specifically, malonaldehyde bis(phenylimine)monohydrochloride (2.6 g, 10 mmol) and 1,3-dimethyl-2-thiobarbituric acid (3.5 g, 20 mmol) are dissolved in acetonitrile (40 mL). To the solution is added triethylamine (2 g, 20 mmol). The reaction mixture is refluxed until the starting materials are completely consumed as indicated by TLC. The mixture is cooled to room temperature, and poured into acidic water (pH 2–3, 350 mL). The resulting suspension is filtered to collect the solid that is washed with cold water and air-dried. The crude product is further purified on a silica gel column using a gradient of dichioromethanol/methanol to give the desired product.

EXAMPLE 2

Measuring Membrane Potentials using $DiSBAC_1(3)$ in Combination with the Fluorescence Imaging Plate Reader (FLIPR™)

This specific example illustrates how to use $DiSBAC_1(3)$ in P2X2 cells in combination with FLIPR™, fluorescent imaging plate reader sold by Molecular Devices Corp. of Sunnyvale, Calif. P2X2 cells are 1321 N1 astrocytoma cells transfected to overexpress the purinergic P2X2 ligand-gated ion channel. P2X2 belongs to a class of purinergic ion channels that pass calcium and sodium in response to purine, including adenosine 5'-triphosphate (ATP). P2X2 cells are propagated and maintained in DME (high glucose), 10% FCS, 1× Pen/Strep and 2 mM L-glutamine. Doubling time is approximately 36 hours. P2X2 cells should be split at a 1 to 2 ratio upon confluence. The cells should be carried for no more than 20 passages. When approaching this limit, a new frozen vial of cells should be resurrected. Following is a typical kit procedure:

1. Plate 40,000 P2X2 cells in 100 μL per well for 96 well plates or 10,000 P2X2 cells in 25 μL per well for 384 well plates for overnight.
2. Prepare 1× Loading Buffer.
2.1 To prepare the 1× Assay Buffer, pipette 10 mL of 10× Reagent Buffer (1× Hanks' Balance Saline Solution+20 mM HPEPES, pH 7.40) and dilute in 90 mL of distilled water. Adjust pH to 7.4 using 1.0 N NaOH and/or 1.0N HCl.
2.2 To prepare 10 mM stock solution of $DiSBAC_1(3)$, dissolve 3.8 mg $DiSBAC_1(3)$ in 1 mL DMSO
2.3 To prepare 10% pluronic acid, dissolve 400 mg pluronic acid in 4 mL water. Heat in 37° C. to complete dissolution.
2.4 To prepare 1× Loading Buffer, add 30 μL of stock $DiSBAC_1(3)$, 8 μL 10% pluronic acid, and 20.0 mg DB71 in the 1× FLIPR assay buffer.
3. Load Cells with 1× Loading Buffer
4. Remove cell plates from the incubator
5. Add 100 μL of 1× Loading Buffer per well of 96-well plates or 25 μL per well of 384-well plates.
6. Incubate plates at 37° C. for 30 minutes.
7. Run the FLIPR Membrane Potential Assay
7.1 Make 5× compound plate prior to running the FLIPR assay. Dissolve 27.5 mg of ATP (Sigma Cat# A3377) in 1 mL of sterile water to make a 50 mM stock solution. Make appropriate dilutions for 100 nM, 1 uM and 10 uM and transfer a minimum of 200 μL to each well of a compound plate.
7.2 Confirm that Membrane Potential Filter is installed. Choose p2x2.fcf for experimental setup in the FLIPR software. Set up the appropriate experiment parameters.
7.3 After incubation, transfer the plates directly to FLIPR and begin the Membrane Potential Assay.
8. Run FLIPR and perform data analysis.

Figure 2:
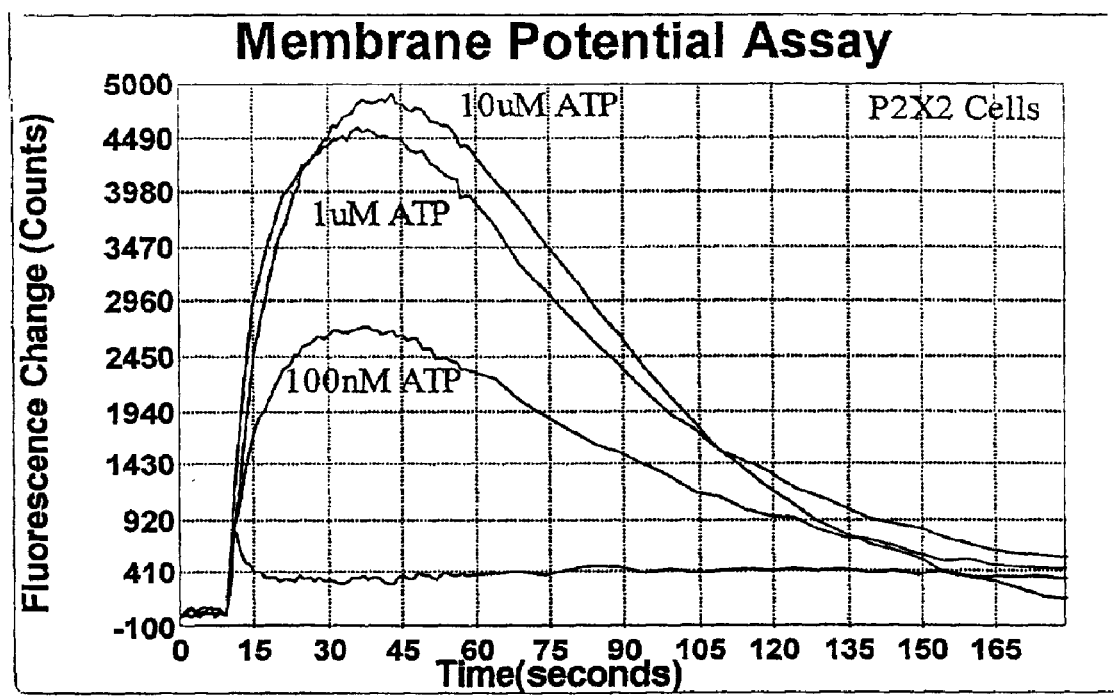
FIG. 2 illustrates the voltage-dependent fluorescence intensity changes of $DiSBAC_1$ (3) in P2X2 cells at different ATP concentrations.

Curve of the ATP dose response should look similar to that shown in FIG. 2; an initial depolarization event depicted as an increase in fluorescence followed by repolarization or decay in signal near baseline. Also, EC50 should be approximately in the 10–100 nM range.

EXAMPLE 3

Measuring Membrane Potentials using $DiBAC_1(3)$ in Combination with a Microscope $DiBAC_1(3)$ is used to measure membrane potential change with a microscope as described by L. M. Loew (Methods in Cell Biology, vol. 38, pp195–209).

EXAMPLE 4

Measuring Membrane Potentials using $DiSBAC_1(3)$ in Combination with Flow Cytometer $DiBAC_1(3)$ is used to measure membrane potential change with a flow cytometer as described by L. M. Loew (Methods in Cell Biology, Vol. 41, Part A, pp195–209).

EXAMPLE 5

Water Solubility and Hydrophobicity Comparison of DiBAC and DiSBAC Dyes $DiSBAC_1(3)$, $DiSBAC_2(3)$, $DiSBAC_3(3)$, $DiSBAC_4(3)$, $DiBAC_1(3)$ and $DiBAC_4(3)$ are dissolved in DMSO (3 mM). The DMSO stock solutions are respectively partitioned in a 1:1 octanol/water mixture. The concentrations of the oxonol dyes in octanol and water layers are determined by absorption spectra. The results are summarized in the following table I. As shown in the table, $DiBAC_1(3)$ and $DiSBAC_1(3)$ are much more hydrophilic than the other oxonol dyes. They also have much better water solubility.

TABLE 1

| Compound | λ$_{max}$ in octanol (nm): | Absorbance in Water: | Absorbance in Octanol: | Absorbance in Water/ Absorbance in Octanol | Relative Values: |
|---|---|---|---|---|---|
| DiBAC$_1$(3) | 495 | 1.297 | 0.3104 | 4.179 | 1 |
| DiBAC$_4$(3) | 497 | 0.002501 | 2.854 | 0.00088 | 0.00021 |
| DiSBAC$_1$(3) | 538 | 0.06147 | 0.9126 | 0.0674 | 1 |
| DiSBAC$_2$(3) | 543 | 0.01143 | 2.187 | 0.0052 | 0.078 |
| DiSBAC$_3$(3) | 544 | 0.002256 | 4.331 | 0.0005 | 0.0077 |
| DiSBAC$_4$(3) | 544 | 0.003318 | 3.226 | <0.0010 | <0.0077 |

EXAMPLE 6

Absorption Comparison of DiBAC and DiSBAC Dyes

Figure 3:
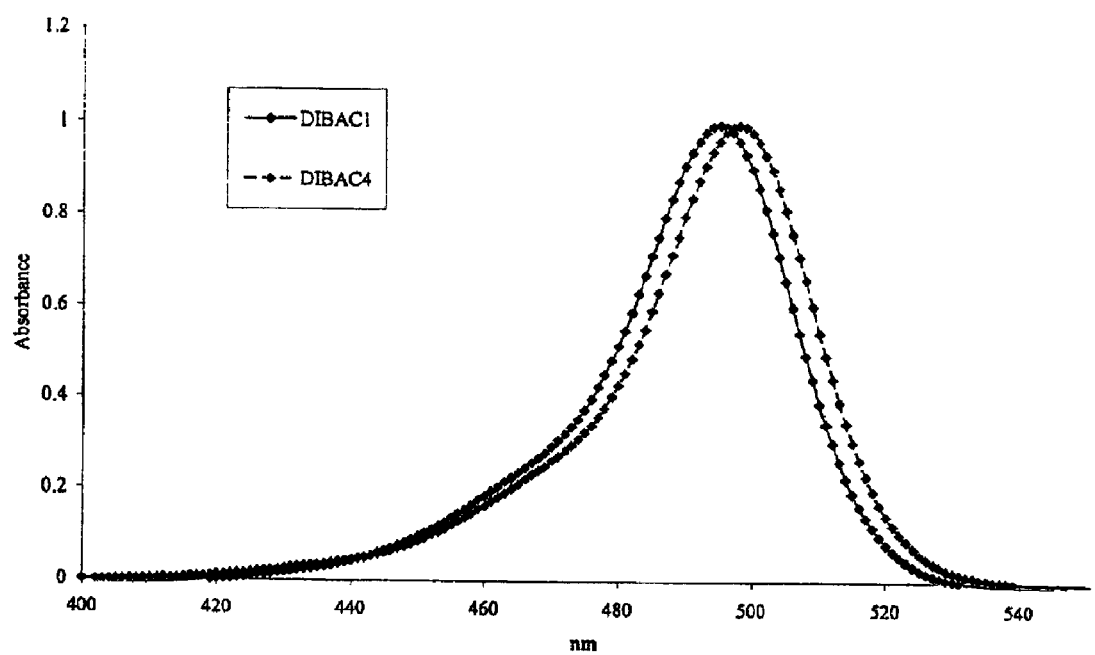
FIG. 3 illustrates the absorption spectra of $DiSBAC_1(3)$, $DiSBAC_2(3)$, $DiSBAC_4(3)$, $DiBAC_1(3)$ and $DiBAC_4(3)$ in 1:1 methanol/water.
Figure 3:
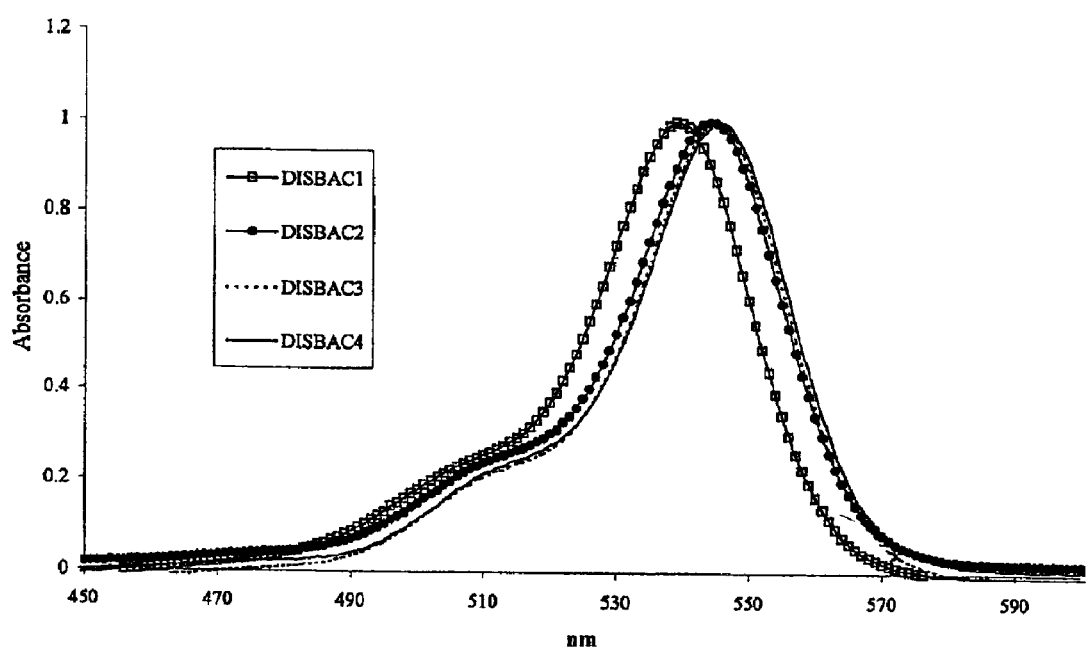

DiSBAC$_1$(3), DiSBAC$_2$(3), DiSBAC$_3$(3), DiSBAC$_4$(3), DiBAC$_1$(3) and DiBAC$_4$(3) are dissolved in methanol (1 mM). The stock solutions are diluted with 1:1 methanol/water, and the absorption spectra are recorded in a spectrophotometer. As shown in FIG. 3, DiBAC$_1$(3) and DiSBAC$_1$(3) possess unexpected blue shift compared to the other oxonol dyes.

EXAMPLE 7

Fluorescence Comparison of DiBAC and DiSBAC Dyes

Figure 4:
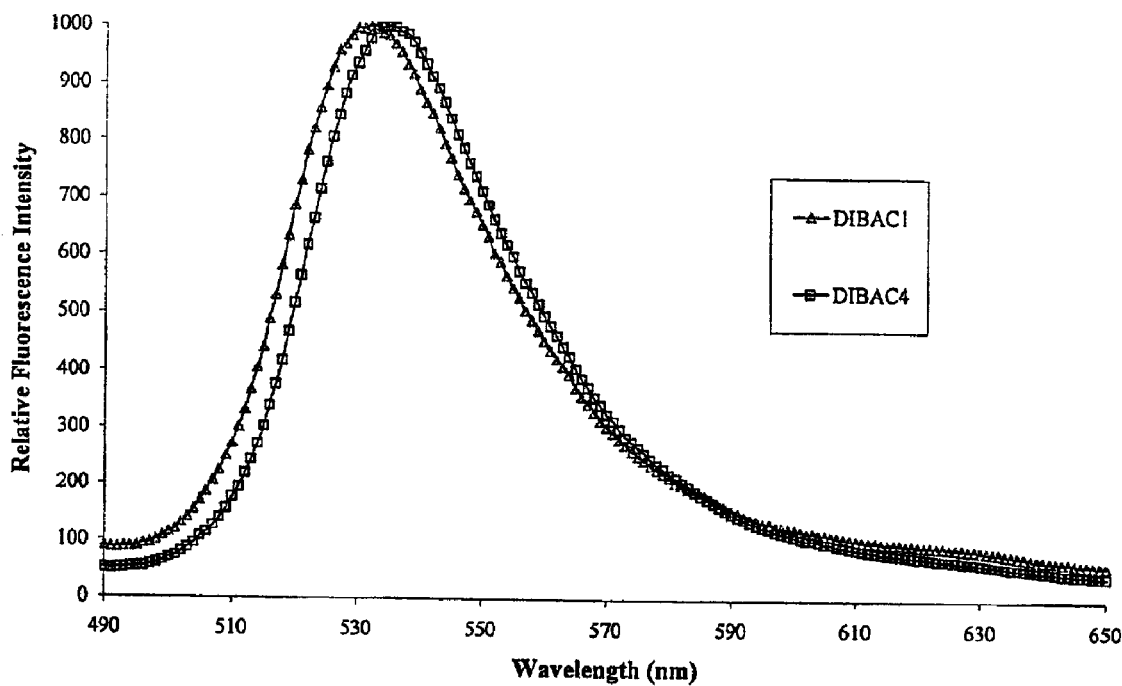
FIG. 4 illustrates the fluorescence spectra of $DiSBAC_1(3)$, $DiSBAC_2(3)$, $DiSBAC_3(3)$, $DiBAC_4(3)$, $DiBAC_1(3)$ and $DiBAC_4(3)$ in 1:1 methanol/water.
Figure 4:
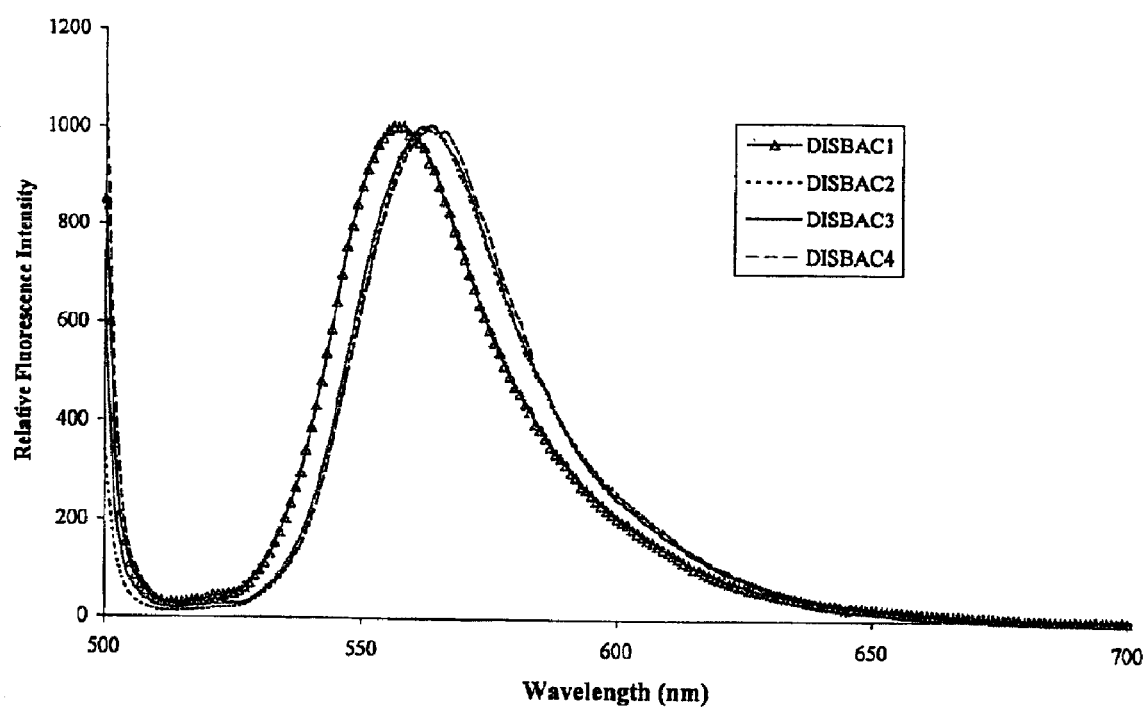

DiSBAC$_1$C$_3$), DiSBAC$_2$(3), DiSBAC$_3$(3), DiSBAC$_4$(3), DiBAC$_1$(3) and DiBAC$_4$(3) are dissolved in methanol (1 mM). The stock solutions are diluted with 1:1 methanol/water, and the absorption spectra are recorded in a fluorometer. As shown in FIG. 4, DiBAC$_1$(3) and DiSBAC$_1$(3) possess unexpected blue shift compared to the other oxonol dyes.

EXAMPLE 8

Fluorescence Response Comparison of DiBAC and DiSBAC Dyes for Sensing Membrane Potentials in FLIPR Assays DiSBAC$_1$(3), DiSBAC$_2$(3), DiSBAC$_3$(3), DiSBAC$_4$(3), DiBAC$_1$(3) and DiBAC$_4$(3) are dissolved in DMSO (1 mM). The stock solutions are respectively used to assay membrane potential changes in the P2X2 cells in combination with FLIPR™ as described in Example 2. The results are summarized in the following table 2.

TABLE 2

| Compounds | Fluorescence Enhancement by 10 μM ATP stimulation (in folds) | Response speed |
|---|---|---|
| DiBAC$_1$(3) | 3.7 | fast |
| DiBAC$_4$(3) | 3.3 | slow |
| DiSBAC$_1$(3) | 108.5 | fast |
| DiSBAC$_2$(3) | 38.6 | moderate |
| DiSBAC$_3$(3) | 14.5 | slow |
| DiSBAC$_4$(3) | 2.3 | slow |

As shown in the table 2, DiSBAC$_1$(3) is much more sensitive, and has faster response to membrane potential change than the rest of the DiSBACs. DIBAC$_1$(3) also has much faster response to membrane potential change than DiBAC$_4$ (3).

EXAMPLE 9

Use of DiSBAC$_1$(3) as a Fluorescent Indicator of Transmembrane Potential

Depolarization of PC 12 Cells

Protocols for transmembrane potential measurements are summarized briefly since they are similar to those given in detail in Example I above. The Bis-(1,3-dimethylthiobarbituric acid) trimethine oxonol, [DiSBAC$_1$(3)], fluorescent reagent may be purchased from Molecular Probes (Eugene, Oreg., USA). The 1. times. Cell-Loading Buffer for DiSBAC$_2$(3), consists of sodium-free Tyrode's Buffer (SFTB), 2.5 uM DiSBAC$_1$(3), and 200 uM Direct Blue 71 (as the fluorescence quencher).

A rat pheochromocytoma (adrenal) cloned cell line, PC$_{12}$, is grown in RPMI 1640 culture medium with 10% fetal calf serum (FCS), 1% penicillin/streptomycin (PS), 2 mM L-glutamine, and 1 mM sodium pyruvate. Cells were grown in suspension, and subsequently centrifuged from growth medium and resuspended in DiSBAC$_2$(3), 1× Cell-Loading Buffer. Approximately 100,000 cells were plated per well in a 96 well microtiter plate pre-coated with poly-D-lysine to enhance cell adhesion, centrifuged at 1000 rpm for 4 minutes, and placed in an incubator for an additional 20 minutes. Cells were not washed with any liquid medium, nor was the 1× Cell-Loading Buffer removed prior to performing fluorescence measurements.

The fluorescently labeled cells were analyzed for changes in membrane potential by using FLIPR™ fluorescent imaging plate reader. Briefly, cells were depolarized with addition of 75 mM potassium gluconate in sodium containing Tyrode's Buffer (SCTB). To inhibit voltage-gated sodium channels cells were previously incubated with 100 uM tetrodotoxin (TTX) for 5 minutes prior to depolarization. The data reveal that cell-depolarization (due to potassium addition) causes increased DiSBAC$_1$(3) fluorescence. Inhibition of sodium channels by TTX results in smaller changes in membrane potential upon potassium addition as indicated by a smaller increase in fluorescence as compared to the positive control (75 mM potassium gluconate without TTX).

The above examples illustrate the present invention and are not intended to limit the invention in spirit or scope.

References

1. Zochowski M, Wachowiak M, Falk C X, Cohen L B, Lam Y W, Antic S, Zecevic D., Imaging membrane potential with voltage-sensitive dyes. *Biol Bull* 198, 1–21 (2000).-

2. Plasek J, Sigler K, Slow fluorescent indicators of membrane potential: a survey of different approaches to probe response analysis. *J Photochem Photobiol B* 33, 101–124 (1996).
3. Loew L M., Characterization of Potentiometric Membrane Dyes. Adv Chem Ser 235, 151 (1994)
4. Wu J-Y, Cohen L B., Fast Multisite Optical Measurement of Membrane Potential. In *Fluorescent and Luminescent Probes for Biological Activity*, Mason W T, Ed., pp. 389–404 (1993).
5. Loew L M., Potentiometric Membrane Dyes. In *Fluorescent and Luminescent Probes for Biological Activity*, Mason W T, $2^{nd}$ Ed. Pp. 210–221 (1999).
6. Smith J C., Potential-sensitive molecular probes in membranes of bioenergetic relevance. *Biochim Biophys Acta* 1016, 1–28 (1990).
7. Gross D, Loew L M., Fluorescent indicators of membrane potential: microspectrofluorometry and imaging. In *Methods Cell Biol* 30, 193–218 (1989).
8. Freedman J C, Novak T S. Optical measurement of membrane potential in cells, organelles, and vesicles. *Methods Enzymol* 172, 102–122 (1989).
9. Bronner C, Landry Y. The use of the potential-sensitive fluorescent probe bisoxonol in mast cells. Biochim Biophys Acta 1070, 321–331 (1991).
10. Shapiro H M. Cell membrane potential analysis. Methods Cell Biol 41, 121–133 (1994).
11. Loew L M. Confocal microscopy of potentiometric fluorescent dyes. Methods Cell Biol 38, 195–209 (1993).
12. Gonzalez J E, Tsien R Y. Improved indicators of cell membrane potential that use fluorescence resonance energy transfer. Chem Biol 4, 269–277 (1997).

What is claimed is:

1. In a method for measuring tranamembrane potential changes in a biological cell, the improvement comprising using compound of Structure I as a potentiometric probe

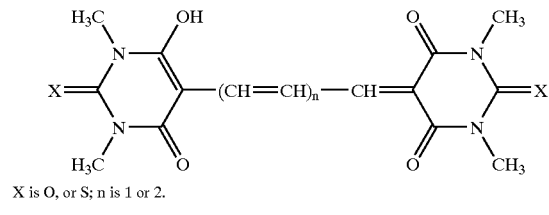

X is O, or S; n is 1 or 2.

2. The method of claim 1 comprising:
  (a) contacting a fluorescent or luminescent compound of structure I with cell membrane;
  (b) stimulating membrane potential changes physically or with a biologically active substance; and
  (c) measuring the fluorescence or luminescence changes.
3. The method of claim 1, wherein the potentiometric probe is used to measure transmembrane potential changes in combination with a second colored reagent.
4. The method of claim 1, wherein the membrane is a plasma membrane of a biological cell.
5. The method of claim 1, wherein the measurement is made in a fluorescence microplate reader.
6. The method of claim 5, wherein the fluorescence microplate reader is a fluorometric plate reader having an integrated pipeting and fluidic system.
7. The method of claim 1, wherein the measurement is made with a fluorescence flow cytometer.
8. The method of claim 1, wherein the measurement is made in a fluorescence microscope.
9. A method of claim 1 wherein a compound of Structure I is used in combination with a second fluorescent indicator.
10. The method of claim 9, wherein the second fluorescent indicator is Indo-1, Fura-2 and Fluo-3, Calcium Green or Fluo-4.

* * * * *